United States Patent
Bolster, Jr.

(10) Patent No.: US 8,463,355 B2
(45) Date of Patent: Jun. 11, 2013

(54) APPARATUS TO ENABLE DISPLAY OF REAL-TIME GRAPHICAL OR NUMERIC INFORMATION WITHIN AN MR IMAGE

(75) Inventor: Bradley Drake Bolster, Jr., Rochester, MN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 846 days.

(21) Appl. No.: 12/481,273

(22) Filed: Jun. 9, 2009

(65) Prior Publication Data
US 2010/0312099 A1 Dec. 9, 2010

(51) Int. Cl.
*A61B 5/05* (2006.01)
(52) U.S. Cl.
USPC .......................................... 600/410

(58) Field of Classification Search
None
See application file for complete search history.

(56) References Cited

U.S. PATENT DOCUMENTS

| | | | |
|---|---|---|---|
| 5,235,279 A * | 8/1993 | Kaufman et al. | 324/309 |
| 6,034,529 A | 3/2000 | Kolem et al. | |
| 6,080,164 A * | 6/2000 | Oshio et al. | 606/130 |
| 7,245,124 B2 * | 7/2007 | Shu et al. | 324/307 |
| 2006/0282168 A1 * | 12/2006 | Sherman et al. | 623/18.12 |

* cited by examiner

*Primary Examiner* — Long V. Le
*Assistant Examiner* — Bradley Impink
(74) *Attorney, Agent, or Firm* — Schiff Hardin LLP

(57) ABSTRACT

In a system or method to enable display of real-time graphical or numeric information within an MR image, at least one display segment having an MR visible substance therein is placed at least partially inside an imaging volume of the MR image.

30 Claims, 4 Drawing Sheets

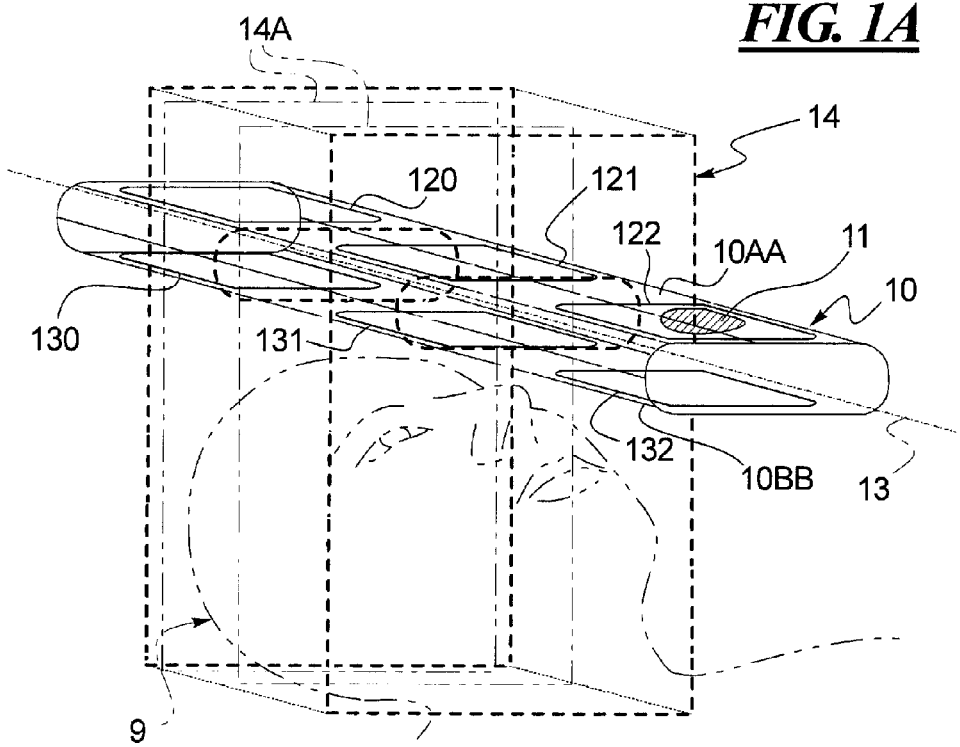
*FIG. 1A*
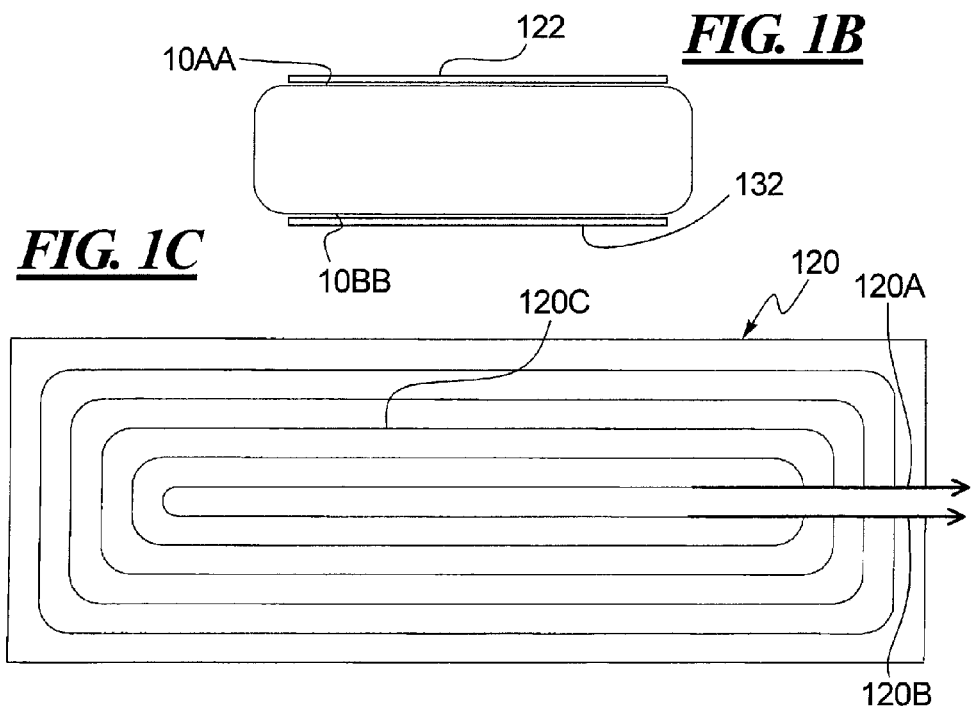
*FIG. 1B*
*FIG. 1C*

APPARATUS TO ENABLE DISPLAY OF REAL-TIME GRAPHICAL OR NUMERIC INFORMATION WITHIN AN MR IMAGE

BACKGROUND

The preferred embodiment relates to magnetic resonance (MR) imaging, and more particularly to studies requiring real-time synchronization between the imaging data and external devices that are part of the study.

Functional MRI studies (fMRI) have moved into regular clinical usage. The basis of the fMRI experiment is to measure and localize the activity in the brain in response to external stimuli or during the performance of certain mental and physical tasks. In addition to providing academic information, these techniques also allow the mapping of certain brain centers in the diagnosis of disease and in pre-surgical planning. As the usage of these techniques has expanded, so has the range of their application. New applications include a patient population which may not be able to perform tasks on a predetermined timescale, forcing the fMRI system to adapt its stimulus presentation to a time course dictated by the patient.

Dynamic imaging studies involving patient motion during the scan have also become more commonplace in diagnostic imaging. A real-time indicator of cycle time or phase during an imaging study has value in later analysis and validation of the data.

Current time-stamps attributed to MR images depend on the scanner, hardware, pulse sequence, and reconstruction scheme used in the acquisition. These values are typically stored in the header of the MR image and are available to an external system once the final images are in a form in which they can be exported. The disadvantage of this technique is that in order to provide time-stamp information in a consistent manner, software at both the pulse sequence and image reconstruction stages must be modified to place the desired timing information in an accessible region of the image header. The ability to modify the software, synchronize with the clocks of the various scanner processors, and get the information in a usable form can be very invasive tasks, especially if multiple pulse sequences are utilized in the experiment.

SUMMARY

It is an object to permit users to be able to inject their own time-stamp information into an MR image frame in a manner that does not require intimate knowledge of the scanner hardware and software systems.

In a system or method to enable display of real-time graphical or numeric information within an MR image, at least one display segment having an MR visible substance therein is placed at least partially inside an imaging volume of the MR image.

BRIEF DESCRIPTION OF THE DRAWINGS

FIG. 1A is a perspective view of a first embodiment to enable display of real-time graphical and numeric information within an MR image by use of a flat tube display segment;

FIG. 1B is an end view of the flat tube used in FIG. 1A with coils on opposite surfaces thereof;

FIG. 1C is a top view of one of the coils of FIGS. 1A and 1B;

DESCRIPTION OF THE PREFERRED EMBODIMENTS

Figure 2A:
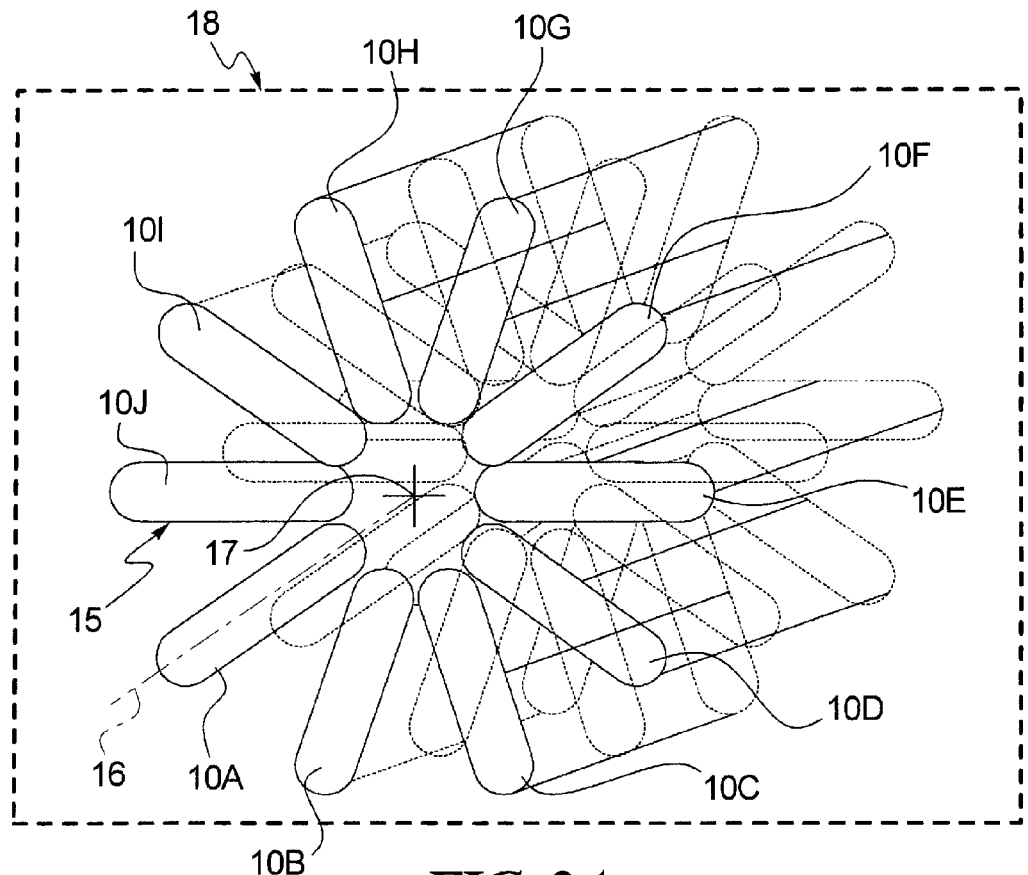
FIG. 2A is second embodiment of display segments combined to form a cylinder to enable display of real-time graphical or numeric information within an MR image.

For the purposes of promoting an understanding of the principles of the invention, reference will now be made to preferred embodiments illustrated in the drawings and specific language will be used to describe the same. It will nevertheless be understood that no limitation of the scope of the invention is thereby intended, and such alterations and further modifications in the illustrated devices and such further applications of the principles of the invention as illustrated as would normally occur to one skilled in the art to which the invention relates are included.

It has long been known that certain substances, both biological and non-biological, once polarized in a static magnetic field will absorb RF energy in a specific frequency range and subsequently release that RF energy. The released energy, when recorded by an adjacent coil and receiver is known in the MRI acquisition as the MR signal. For the purposes of the preferred embodiments described hereafter, such substances are defined hereafter as being "MR visible." Further, the frequency of both the absorbed and released RF energy is directly proportional to the strength of the magnetic field experienced by the nuclei of the MR visible substance. This frequency is known as the Larmour frequency and for the purposes of describing the preferred embodiments hereafter, this is referred to hereafter as the "frequency of the nuclei being imaged" and describe coils sensitive (or tuned) to this frequency as "resonant at the frequency of the nuclei being imaged." With the preferred embodiments, to enable synchronization without invasive coupling to the MR imaging system, time-stamps or other graphical representations of events within the image acquired by the MRI scanner.

In the first embodiment as shown in FIG. 1A, a display segment 10 is formed as a flat tube filled with an MR visible substance 11 resonant at or near a frequency of a nucleus being imaged. A plurality of coils 120, 121, 122 are placed on a top flat surface 10AA and a plurality of opposite lying coils 130, 131, 132 are placed on a bottom flat surface 10BB of tube 10 in order to create a plurality of Maxwell pairs (in this case three pairs) across the imagable volume inside the tube (see FIGS. 1A, 1B, 1C). When energized, the pairs of oppositely positioned coils will create a plurality of large local field gradients along a length of the tube 10 preventing a coherent MR signal from the tube during the imaging. This energized state represents the "OFF" state for the display element. The "ON" state is realized when the coils are de-energized. In this state, the coils are tuned so as to be resonant about a Larmour frequency of the substance 11 with which the tube is filled, thus enhancing the MR signal from the tube through inductive coupling. The axis 13 of the display segment 10 is oriented normal to imaging planes 14A of interest in imaging volume 14 so as to be visible in every image in the image stack.

As further shown in FIG. 1A, the imaging volume 14 for the MR image has located therein a volume of interest 9 comprising at least a portion of a person, animal, or object being imaged. And also as shown in FIG. 1A, the display segment 10 is placed at least partially inside the imaging volume 14.

Thus the MR signals originating from both the display segment and from the volume of interest 9, such as a person's head as shown in FIG. 1A, then can be utilized to simultaneously show a slice of the display segment 10 adjacent to or along with a slice of the volume of interest when these slices are viewed by the MR user.

As shown in FIG. 1C, the coil 120, for example, is formed of windings 120C and is energized via leads 120A, 120B.

Figure 2B:
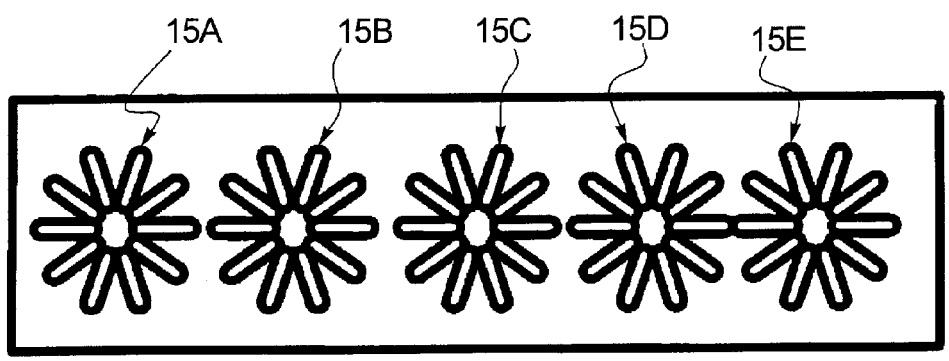
FIG. 2B shows in a front view an array of a plurality of the cylinders shown in FIG. 2A to represent multiple digits in a display.

In the second embodiment shown in FIG. 2A, ten display segments 10A-10J as described in the first embodiment are oriented to form a cylinder 15, with short axis 16 of each segment projecting radially from a center 17 of the cylinder 15. The cylinder 15 is oriented normal to the imaging planes 18 of interest so as to be visible in every image In the image stack as a ten element clock face. An array of these cylinders can be grouped together to represent multiple digits 15A-15E in a base ten display as shown in FIG. 2B. Electronics are constructed to drive the display which converts timing signals from an onboard clock or externally generated signals to currents selectively applied to the individual segments so as to render a recognizable display of the input signals in the MRI images being acquired.

Figure 3A:
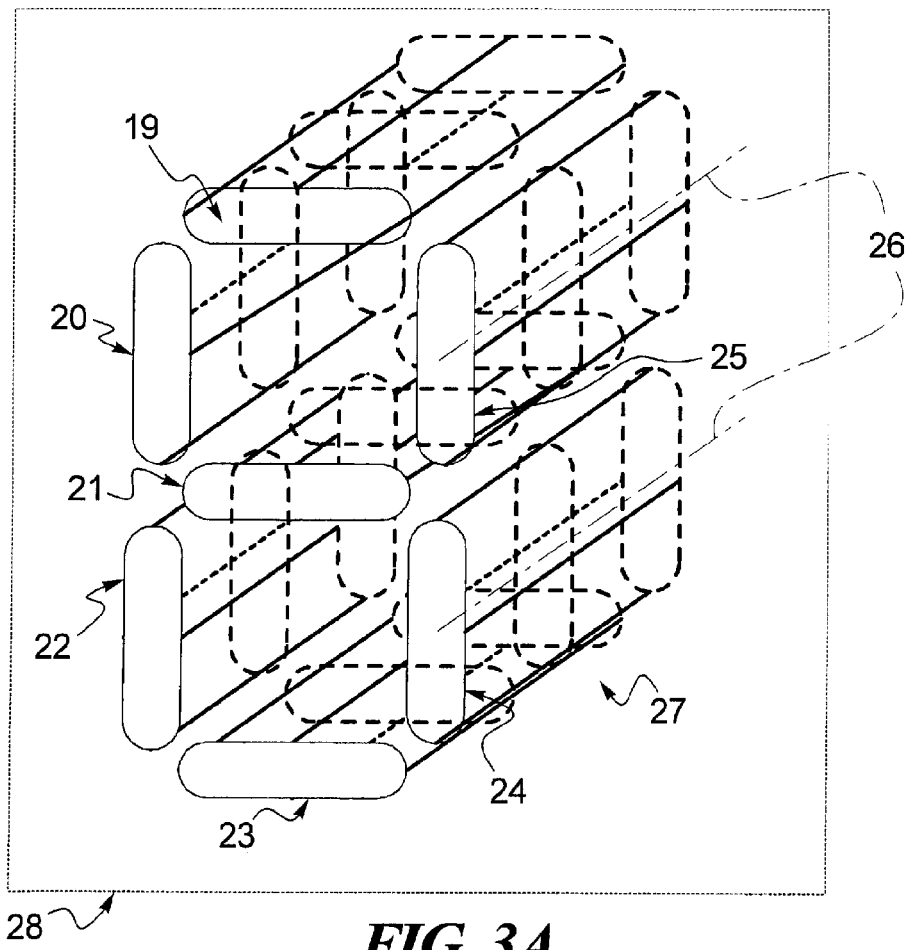
FIG. 3A is a perspective view of a third embodiment of an image display for a letter or number formed from a plurality of segments for real-time graphical or numeric information within an MR image.
Figure 3B:
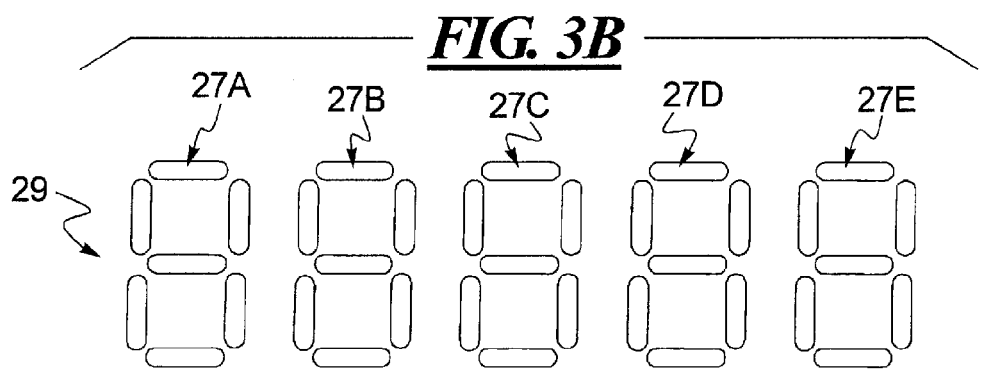
FIG. 3B is a front view of an array of multiple displays of the type shown in FIG. 3A.

In a third embodiment shown in FIG. 3A, seven display segments 19-25 as described in the first embodiment are arranged with long axes 26 parallel to yield a seven segment display 27 when viewed end on. These long axes 26 are oriented normal to the imaging planes 28 of interest so as to be visible in every image. An array 29 of five of these seven segment displays 27A-27E can be grouped together to represent multiple numerical or alphabetic digits as shown in FIG. 3B. Electronics are constructed to drive the display which converts timing signals from an onboard clock or externally generated signals to currents selectively applied to the individual elements so as to render a recognizable display of the input signals in the MRI images being acquired.

Figure 4:
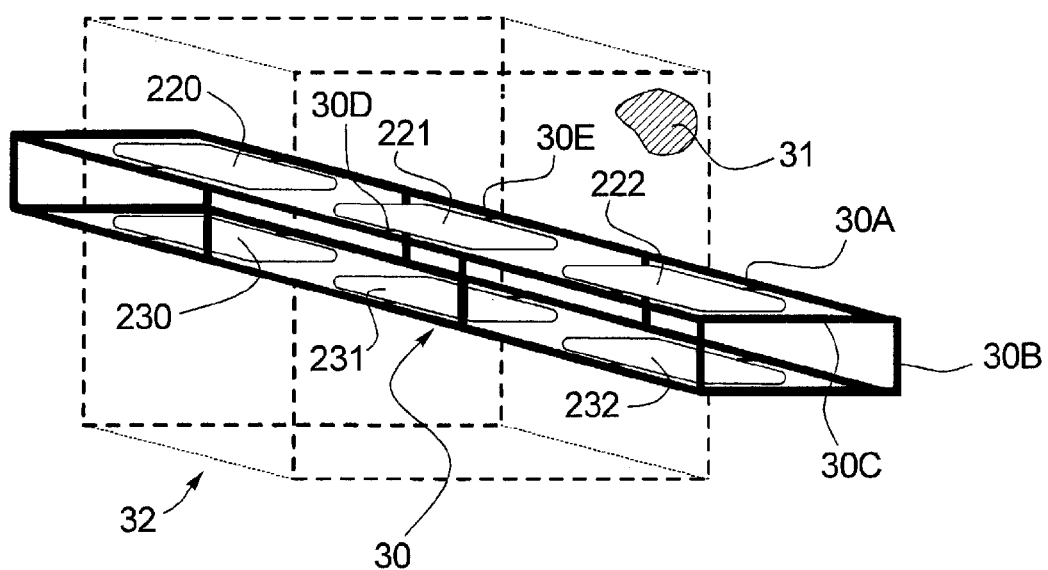
FIG. 4 is a perspective view of a fourth embodiment for display of real-time graphical or numeric information within an MR image.

In a fourth embodiment shown in FIG. 4, as opposed to employing flat tubes as shown in the first embodiment, Maxwell coil pairs 220, 230; 221, 231; and 222, 232 are provided at an open frame 30 which is immersed in the imaging volume 32 and then in an MR visible substance 31. The open frame 30 is constructed of a plurality of frame struts 30A, 30B, and 30C with the areas between the frame struts being open and thus forming entrance apertures through which the immersion fluid enters within the frame. The coils 220, 221, 222 are supported by frame support members 30D and 30E, for example. Accompanying electronics are then designed such that display elements to which current is selectively applied to the Maxwell coils are considered "ON" and those to which current is not applied are considered OFF. In this embodiment the coil pairs are tuned or decoupled to a frequency well away from an imaging frequency during the "OFF" state so that elements in this OFF state do not appear bright relative to the background. In the "ON" state, the elements appear dark relative to the light background. In this FIG. 4 embodiment, a clock face pattern as shown in FIGS. 2 and 3 may be employed.

Figure 5:
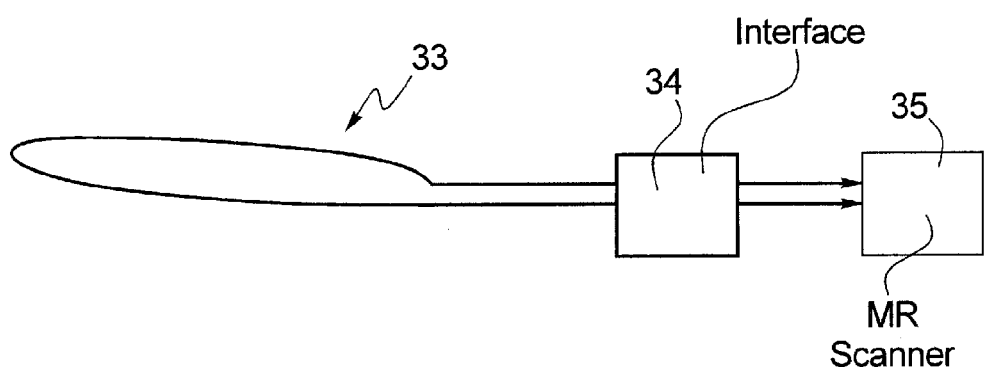
FIG. 5 is a perspective view showing the use of a separate RF surface coil at the imaging volume containing the display segments.

As shown in FIG. 5 if necessary, a separate RF surface coil or coils 33 may be included in the display construction at the imaging volume 14 (or 32 in FIG. 4) described in either the second, third, or fourth embodiments and which is tuned to a Larmour frequency of the substance with which the tube is filled. The signal from this coil which is connected through interface 34 to the MR scanner 35, is added as a separate receive channel by the MR scanner 35 and enables the display to be used when the display array cannot be located inside the imaging coil being utilized in the imaging.

While preferred embodiments have been illustrated and described in detail in the drawings and foregoing description, the same are to be considered as illustrative and not restrictive in character, it being understood that only the preferred embodiments have been shown and described and that all changes and modifications that come within the spirit of the invention both now or in the future are desired to be protected.

I claim as my invention:

1. A system to enable display of real-time alphabetic and/or numeric changeable message information within an MR image of a volume of interest comprising at least a portion of a person, animal, or object being imaged, comprising:
    an imaging volume which defines a region in a magnetic field of an MR machine in which imaging planes are located for constructing the MR image and within which is located said volume of interest which said imaging planes intersect;
    at least one tube or frame display segment having an MR visible substance therein, said display segment being placed at least partially inside said imaging volume to provide said changeable message information during MR imaging; and
    said display segment having at least one respective coil on each of opposite sides of the display segment to create a Maxwell pair across the display segment inside the imaging volume.

2. The system of claim 1 wherein the MR visible substance is adapted to be resonant at or near a frequency of a nucleus being imaged.

3. The system of claim 1 wherein said display segment comprises a flat tube having said at least one respective coil on each opposite surface of the display segment.

4. A system to enable display of real-time graphical or numeric information within an MR image of a volume of interest comprising at least a portion of a person, animal, or object being imaged, comprising:
    an imaging volume which defines a region in a magnetic field of an MR machine in which imaging planes are located for constructing the MR image and within which is located said volume of interest which said imaging planes intersect;
    at least one tube or frame display segment having an MR visible substance therein, said display segment being placed at least partially inside said imaging volume;
    said display segment comprises a flat tube having at least one respective coil on each opposite surface of the display segment to create a Maxwell pair across the display segment inside the imaging volume; and
    a plurality of coils are placed on each of said opposite surfaces of the display segment so as to create a plurality of said Maxwell pairs across the display segment inside the imaging volume.

5. The system of claim 4 wherein when energized, the Maxwell pairs are adapted to create a plurality of large local field gradients along a length of the display segment preventing a coherent MR signal from the display segment during the imaging, the energized state representing an "OFF" state for the display segment, and an "ON" state being provided when the coils are de-energized.

6. The system of claim 3 wherein a longitudinal axis of the flat tube runs perpendicular to an imaging plane of the imaging volume.

7. A system to enable display of real-time graphical or numeric information within an MR image of a volume of interest comprising at least a portion of a person, animal, or object being imaged, comprising:
- an imaging volume which defines a region in a magnetic field of an MR machine in which imaging planes are located for constructing the MR image and within which is located said volume of interest which said imaging planes intersect;
- at least one tube or frame display segment having an MR visible substance therein, said display segment being placed at least partially inside said imaging volume;
- said display segment comprises a flat tube having at least one respective coil on each opposite surface of the display segment to create a Maxwell pair across the display segment inside the imaging volume; and
- a plurality of said flat tube segments are arranged like spokes of a wheel about a center to form a cylinder such that short axes of the segments run radially outwardly from said center of the cylinder defined by said segments and the longitudinal axes of said segments run perpendicular to one or more imaging planes in the imaging volume.

8. The system of claim 3 wherein a plurality of said flat tube display segments are arranged with their longitudinal axes parallel and are grouped to form a number, a letter, or a symbol when viewed from an end of the display segments.

9. A system to enable display of real-time graphical or numeric message information within an MR image of a volume of interest comprising at least a portion of a person, animal, or object being imaged, comprising:
- an imaging volume which defines a region in a magnetic field of an MR machine in which imaging planes are located for constructing the MR image and within which is located the said volume of interest which said imaging planes intersect;
- at least one tube or frame display segment having an MR visible substance therein, said display segment being placed at least partially inside said imaging volume; and
- the display segment comprises a frame having at least one aperture and at least partially located in said imaging volume with Maxwell coil pairs being provided along opposite surfaces thereof and wherein said imaging volume is at least partially filled with said MR visible substance which is also present at least partially inside said frame which is at least partially immersed in said MR visible substance.

10. The system of claim 9 wherein when energized, the Maxwell pairs are adapted to create a plurality of large local field gradients along a length of the display segment preventing a coherent MR signal from the display segment during the imaging, the energized state representing an "ON" state for the display segment, and an "OFF" state being provided when the coils are de-energized.

11. The system of claim 9 wherein said frame has a short axis and a longitudinal axis, and a plurality of said frames are arranged like spokes of a wheel about a center to form a cylinder such that the short axes of the frames run radially outwardly from said center of the cylinder defined by said frames and the longitudinal axes of said frames run perpendicular to one or more imaging planes in the imaging volume.

12. The system of claim 9 wherein said frame has a longitudinal axis and a plurality of said frames are arranged with their longitudinal axes parallel and are grouped to form a number, a letter, or a symbol when viewed from an end of the frames.

13. The system of claim 1 wherein a local RF coil is arranged adjacent to or around said imaging volume.

14. The system of claim 13 wherein the RF coil is tuned to a Larmour frequency of said MR visible substance in said display segment.

15. The system of claim 14 wherein the signal from said RF coil is connected to an image scanner generating said MR image.

16. A method to enable display of real-time alphabetic and/or numeric changeable message information within an MR image of a volume of interest comprising at least a portion of a person, animal, or object being imaged, an imaging volume which defines a region in a magnetic field of an MR machine in which imaging planes are located for constructing the MR image and having located therein said volume of interest which said imaging planes intersect, comprising the steps of:
- providing at least one tube or frame display segment having an MR visible substance therein, said display segment being placed at least partially inside said imaging volume to provide said changeable message information during MR imaging, and wherein at least one respective coil is provided on opposite sides of the display segment to create a Maxwell pair across the display segment inside the imaging volume; and
- displaying with said display segment information relating to the MR image.

17. The method of claim 16 wherein the MR visible substance is resonant at or near a frequency of a nucleus being imaged.

18. The method of claim 16 wherein said display segment comprises a flat tube having said at least one respective coil on each opposite surface of the display segment.

19. A method to enable display of real-time graphical or numeric information within an MR image of a volume of interest comprising at least a portion of a person, animal, or object being imaged, an imaging volume which defines a region in a magnetic field of an MR machine in which imaging planes are located constructing the MR image and having located therein said volume of interest which said imaging planes intersect, comprising the steps of:
- providing at least one tube or frame display segment having an MR visible substance therein, said display segment being displaced at least partially inside said imaging volume, said display segment comprising a flat tube having said at least one respective coil on each opposite surface of the display segment to create a Maxwell pair across the display segment inside the imaging volume, and a plurality of coils being placed on each of said opposite surfaces of the display segment so as to create a plurality of said Maxwell pairs across the display segment inside the imaging volume to control said activation of the MR visible substance; and
- displaying said display segment information relating to the MR image.

20. The method of claim 19 wherein when energized, the Maxwell pairs are adapted to create a plurality of large local field gradients along a length of the display segment preventing a coherent MR signal from the display segment during imaging, the energized state representing an "OFF" state for the display segment, and an "ON" state being provided when the coils are de-energized.

21. The method of claim 18 wherein a longitudinal axis of the flat tube runs perpendicular to an imaging plane of the imaging volume.

22. A method to enable display of real-time graphical or numeric information within an MR image of a volume of interest comprising at least a portion of a person, animal, or object being imaged, an imaging volume which defines a region in a magnetic field of an MR machine in which imaging planes are located constructing the MR image and having located therein said volume of interest which said imaging planes intersect, comprising the steps of:
providing at least one tube or frame display segment to having an MR visible substance therein, said display segment being displaced at least partially inside said imaging volume, said display segment comprising a flat tube having said at least one respective coil on each opposite surface of the display segment to create a Maxwell pair across the display segment inside the imaging volume, and a plurality of said flat tube segments being arranged like spokes of a wheel about a center to form a cylinder such that short axes of the segments run radially outwardly from said center of the cylinder defined by said segments and the longitudinal axes of said segments run perpendicular to one or more imaging planes in the imaging volume; and
displaying said display segment information relating to the MR image.

23. The method claim 18 wherein a plurality of said flat tube display segments are arranged with their longitudinal axes parallel and are grouped to form a number, a letter, or a symbol when viewed from an end of the display segments.

24. A method to enable display of real-time graphical or numeric information within an MR image of a volume of interest comprising at least a portion of a person, animal, or object being imaged, an imaging volume which defines a region in a magnetic field of an MR machine in which imaging planes are located constructing the MR image and having located therein said volume of interest which said imaging planes intersect, comprising the steps of:
providing at least one tube or frame display segment having an MR visible substance therein, said display segment being placed at least partially inside said imaging volume, and the display segment comprising a frame having at least one aperture and at least partially located in said imaging volume with Maxwell coil pairs being provided along opposite surfaces thereof and wherein said imaging volume is at least partially filled with said MR visible substance which is also present at least partially inside said frame which is at least partially immersed in said MR visible substance; and
displaying with said display segment information relating to the MR image.

25. The method of claim 24 wherein when energized, the Maxwell pairs are adapted to create a plurality of large local field gradients along a length of the display segment preventing a coherent MR signal from the display segment when imaging is not occurring, the energized state representing an "ON" state for the display segment, and an "OFF" state being provided when the coils are de-energized during imaging.

26. The method of claim 24 wherein said frame has a short axis and a longitudinal axis, and a plurality of said frames are arranged like spokes of a wheel about a center to form a cylinder such that the short axes of the frames run radially outwardly from said center of the cylinder defined by said frames and the longitudinal axes of said frames run perpendicular to one or more imaging planes in the imaging volume.

27. The method of claim 24 wherein said frame has a longitudinal axis and a plurality of said frames are arranged with their longitudinal axes parallel and are grouped to form a number, a letter, or a symbol when viewed from an end of the frames.

28. The method of claim 16 wherein a local RF coil is arranged adjacent to or around said imaging volume.

29. The method of claim 28 wherein the RF coil is tuned to a Larmour frequency of said MR visible substance in said display segment.

30. The method of claim 29 wherein the signal from said RF coil is connected to an image scanner generating said MR image.

* * * * *